(12) United States Patent
Hayashi et al.

(10) Patent No.: US 6,222,046 B1
(45) Date of Patent: *Apr. 24, 2001

(54) TETRAALKYLFLUOROFORMAMIDINIUM TRIFLUOROACETATE AND PREPARATION PROCESS OF SAME

(75) Inventors: Hidetoshi Hayashi; Hiroshi Sonoda; Kenichi Goto; Kouki Fukumura; Junko Naruse; Teruyuki Nagata, all of Fukuoka-ken (JP)

(73) Assignee: Mitsui Chemicals, Inc. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/370,213

(22) Filed: Aug. 9, 1999

(30) Foreign Application Priority Data

Aug. 19, 1998 (JP) .................................................. 10-233122

(51) Int. Cl.$^7$ ...................... C07D 239/02; C07D 401/06; C07C 249/02; C07C 251/02; C07C 69/63
(52) U.S. Cl. .................. 548/347.1; 546/186; 548/352.1; 560/227; 562/202; 562/512; 562/605; 564/270
(58) Field of Search ............................. 548/347.1, 352.1; 562/202, 512, 605; 564/240; 560/227

(56) References Cited

U.S. PATENT DOCUMENTS

| | | | |
|---|---|---|---|
| 5,011,937 | * | 4/1991 | Govindan .............................. 548/354 |
| 5,712,418 | * | 1/1998 | Carpino et al. ....................... 564/225 |
| 5,856,513 | * | 1/1999 | Ue et al. .............................. 548/347.1 |

FOREIGN PATENT DOCUMENTS 4-308538  10/1991 (JP).

OTHER PUBLICATIONS

Farcasiu et al, "Secondary and Tertiary 2–Methylbutyl Cations. 1. Trifluoroacetolysis of 3–Methyl–2–butyl Tosylate", Journal of Organi Chemistry, vol. 59., No. 1, pp. 154–162, 1994.

* cited by examiner

Primary Examiner—Floyd D. Higel
(74) Attorney, Agent, or Firm—Burns, Doane, Swecker, & Mathis, L.L.P.

(57) ABSTRACT

The invention has disclosed a trifluoroacetoxylation agent and a preparation process of the agent, which is safe and ease to handle, very useful in industry, and represented by the formula (1);

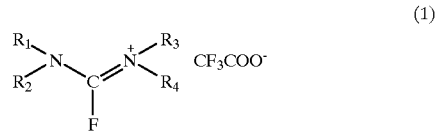

(1)

wherein $R_1$ to $R_4$ are a substituted or unsubstituted, saturated or unsaturated alkyl group or a substituted or unsubstituted aryl group and can be the same or different, $R_1$ and $R_2$ or $R_3$ and $R_4$ can bond to form a ring containing a nitrogen atom or a nitrogen atom and other hetero atoms, and $R_1$ and $R_3$ can bond to form a ring containing a nitrogen atom or a nitrogen atom and other hetero atoms.

9 Claims, No Drawings

TETRAALKYLFLUOROFORMAMIDINIUM TRIFLUOROACETATE AND PREPARATION PROCESS OF SAME

BACKGROUND OF THE INVENTION

1. Field of the Invention

The present invention relates to a novel fluorine containing compound and a preparation process of the same. More specifically, the invention relates to a novel fluorine containing compound, tetraalkylfluoroformamidinium trifluoroacetate and a preparation process of the compound.

2. Prior Art of the Invention

In a conventional method for preparing trifluoroacetate ester, the compounds such as trifluoroacetic acid, trifluoroacetyl chloride and trifluoroacetic anhydride have been principally used.

The trifluoroacetate ester can be prepared by an esterification reaction using these compounds.

The process for preparing a trifluoroacetate ester by using trifluoroacetic acid includes, for example, a process for preparing the ester by condensation of trifluoroacetic acid with alcohol.

As an example of such process, J. Am. Chem, Soc., 79, 54 (1957) has reported a process for reacting alcohol with excess trifluoroacetic acid in the presence of a sulfuric acid catalyst and successively washing resultant ester with water to obtain trifluoroacetate ester. However, the process leads to partial hydrolysis of ester in the course of washing, and further, it is difficult to recover excess trifluoroacetic acid from an aqueous layer. Thus, application of the process in industry cannot be carried out with ease.

The process for preparing a trifluoroacetate ester by using trifluoroacetyl chloride includes a process for reaction of trifluoroacetyl chloride with alcohol in the presence of a basic catalyst. The process can prepare trifluoroacetate ester under mild condition in high yields as compared with the above case using trifluoroacetic acid. However, the process also requires a complicated method for recovery and reuse for hydrochloride of the base and has a problem on storage due to hydrolyzability of trifluoroacetyl chloride.

The process by use of trifluoroacetic anhydride can prepare trifluoroacetate ester under mild conditions due to high reactivity of trifluoroacetic anhydride. However, trifluoroacetic anhydride is expensive and thus application of the process in industry is difficult in view of economy.

SUMMARY OF THE INVENTION

The object of the invention is to provide a novel fluorine-containing compound, tetraalkylfluoroformamidinium trifluoroacetate, which is useful for a trifluoroacetoxylation reaction and a preparation process of the compound.

As a result of an intensive investigation in order to solve these subjects, the present inventors have found a novel compound represented by the formula (1):

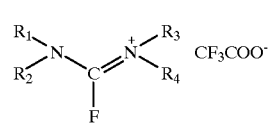

(1)

wherein $R_1$ to $R_4$ are a substituted or unsubstituted, saturated or unsaturated alkyl group or a substituted or unsubstituted aryl group and can be the same or different, $R_1$ and $R_2$ or $R_3$ and $R_4$ can bond to form a ring containing a nitrogen atom or a nitrogen atom and other hetero atoms, and $R_1$ and $R_3$ can bond to form a ring containing a nitrogen atom or a nitrogen atom and other hetero atoms, and that the novel compound is excellent as a novel anion carrier, that is, a trifluoroacetoxylation agent and is useful for preparation of trifluoroacetate ester. And further, they have found that the application of the novel compound to a trifluoroacetoxylation reaction can be carried out in high safety and with ease without requiring specific equipment or technique.

The compound represented by the formula (1) can be prepared by reacting an alkali metal salt of trifluoroacetic acid with a compound represented by the formula (4);

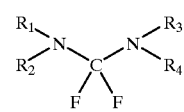

(4)

wherein $R_1$ to $R_4$ are a substituted or unsubstituted, saturated or unsaturated alkyl group or a substituted or unsubstituted aryl group and can be the same or different, $R_1$ and $R_2$ or $R_3$ and $R_4$ can bond to form a ring containing a nitrogen atom or a nitrogen atom and other hetero atoms, $R_1$ and $R_3$ can bond to form a ring containing a nitrogen atom or a nitrogen atom and other hetero atoms, one of the fluorine atoms can form an ion pair as anion.

Thus, no specific equipment or technique is required at all and preparation can be carried out with safety in industry.

Further, the compound represented by the formula (4) can be prepared from an intermediate compound represented by the formula (5);

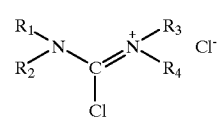

(5)

wherein $R_1$ to $R_4$ are a substituted or unsubstituted, saturated or unsaturated alkyl group or a substituted or unsubstituted aryl group and can be the same or different, $R_1$ and $R_2$ or $R_3$ and $R_4$ can bond to form a ring containing a nitrogen atom or a nitrogen atom and other hetero atoms, and $R_1$ and $R_3$ can bond to form a ring containing a nitrogen atom or a nitrogen atom and other hetero atoms, and a chlorine anion can covalently bond with the carbon atom having a chlorine atom. Urea is the raw material of the intermediate compound of the formula (5).

The inventors have also found that, after finishing the trifluoroacetoxylation reaction, the trifluoroacetoxylation agent can be recovered in the form of a urea derivative and reused in economy.

That is, one aspect of the invention is:

1) A compound represented by the formula (1);

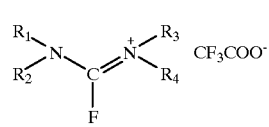

(1)

wherein $R_1$ to $R_4$ are a substituted or unsubstituted, saturated or unsaturated alkyl group or a substituted or unsubstituted aryl group and can be the same or different, $R_1$ and $R_2$ or $R_3$ and $R_4$ can bond to form a ring containing a nitrogen atom or a nitrogen atom and other hetero atoms, and $R_1$ and $R_3$ can bond to form a ring containing a nitrogen atom or a nitrogen atom and other hetero atoms.

2) A compound according to 1) wherein the compound represented by the formula (1) is a compound represented by the formula (2);

$$\text{CH}_3-\text{N}\underset{\underset{F}{|}}{\overset{(CH_2)_a}{\underset{C}{\diagup}}}\overset{+}{\text{N}}-\text{CH}_3 \quad \text{CF}_3\text{COO}^- \tag{2}$$

wherein a is an integer of 2 or 3.

3) A compound according to 1) wherein the compound represented by the formula (1) is 2-fluoro-1,3-dimethylimidazolinium trifluoroacetate represented by the formula (3);

$$\text{CH}_3-\text{N}\underset{\underset{F}{|}}{\overset{\frown}{\underset{C}{\diagup}}}\overset{+}{\text{N}}-\text{CH}_3 \quad \text{CF}_3\text{COO}^- \tag{3}$$

4) A preparation process of a compound represented by the formula (1);

$$\underset{R_2}{\overset{R_1}{\diagdown}}\text{N}\underset{\underset{F}{|}}{\overset{}{\underset{C}{\diagup}}}\overset{+}{\text{N}}\underset{R_4}{\overset{R_3}{\diagup}} \quad \text{CF}_3\text{COO}^- \tag{1}$$

wherein $R_1$ to $R_4$ are the same as above, comprising reacting a compound represented by the formula (4);

$$\underset{R_2}{\overset{R_1}{\diagdown}}\text{N}\underset{\underset{F}{|}\underset{F}{|}}{\overset{}{\underset{C}{\diagup}}}\text{N}\underset{R_4}{\overset{R_3}{\diagup}} \tag{4}$$

wherein $R_1$ to $R_4$ are the same as above, and one of the fluorine atoms can form an ion pair as anion, with an alkali metal salt of trifluoroacetic acid.

5) A preparation process according to 4) wherein the compound represented by the formula (1) is a compound represented by the formula (2);

$$\text{CH}_3-\text{N}\underset{\underset{F}{|}}{\overset{(CH_2)_a}{\underset{C}{\diagup}}}\overset{+}{\text{N}}-\text{CH}_3 \quad \text{CF}_3\text{COO}^- \tag{2}$$

wherein a is an integer of 2 or 3, and the compound represented by the formula (4) is a compound represented by the formula (4-1);

$$\text{CH}_3-\text{N}\underset{\underset{F}{|}\underset{F}{|}}{\overset{(CH_2)_a}{\underset{C}{\diagup}}}\text{N}-\text{CH}_3 \tag{4-1}$$

wherein a is an integer of 2 or 3.

6) A preparation process according to 4) wherein the compound represented by the formula (1) is a compound represented by the formula (3):

$$\text{CH}_3-\text{N}\underset{\underset{F}{|}}{\overset{\frown}{\underset{C}{\diagup}}}\overset{+}{\text{N}}-\text{CH}_3 \quad \text{CF}_3\text{COO}^- \tag{3}$$

and the compound represented by the formula (4) is a compound represented by the formula (4-2);

$$\text{CH}_3-\text{N}\underset{\underset{F}{|}\underset{F}{|}}{\overset{\frown}{\underset{C}{\diagup}}}\text{N}-\text{CH}_3 \tag{4-2}$$

7) A trifluoroacetoxylation agent according to one of 1) to 3).

The present invention has enabled to provide a novel fluorine containing compound, tetraalkylfluoroformamidinium trifluoroacetate which is safe, ease to handle, very useful in industry and can be used for an industrial production of trifluoroacetate ester.

The compound of the invention can eliminate various problems in the conventional preparation processes of fluorine compounds and is effective for the preparation of fluorine compound in industry.

PREFERRED EMBODIMENT OF THE INVENTION

The invention will be illustrated in detail hereafter.

The compound of the invention, that is, the compound which is useful as the trifluoroacetoxylation agent of the invention is tetraalkylfluoroformamidinium trifluoroacetate represented by the above formula (1), preferably the compound represented by the formula (2), more preferably the compound represented by the formula (3).

In the formula (1), $R_1$ to $R_4$ are a substituted or unsubstituted, saturated or unsaturated alkyl group or a substituted or unsubstituted aryl group, preferably an alkyl or aryl group having 1 to 6 carbon atoms. The alkyl group can be a straight-chain or branched-chain and includes, for example, a methyl, ethyl, n-propyl, isopropyl, n-butyl, i-butyl, t-butyl, n-pentyl, n-hexyl, cyclohexyl, phenyl, naphthyl, methylphenyl, ethylphenyl and dimethylphenyl group. Those groups can be the same or different.

$R_1$ and $R_2$ or $R_3$ and $R_4$ can individually bond to form a ring containing a nitrogen atom or a nitrogen atom and other hetero atoms, and having 3 to 5 carbon atoms.

Examples of these rings include a pyrrolidine ring and piperidine ring.

Further, $R_1$ and $R_3$ can bond to form a five or six membered ring containing a nitrogen atom or a nitrogen atom and other hetero atoms. Examples of such rings include an imidazolidine ring.

Specific compounds represented by the formula (1) include following compounds. However, the invention is not limited by these exemplified compounds.

Tetramethyl-2-fluoroformamidinium trifluoroacetate,
Tetraethyl-2-fluoroformamidinium trifluoroacetate,
Tetra-n-propyl-2-fluoroformamidinium trifluoroacetate,
Tetraisopropyl-2-fluoroformamidinium trifluoroacetate,
Tetra-n-butyl-2-fluoroformamidinium trifluoroacetate,
Tetra-n-pentyl-2-fluoroformamidinium trifluoroacetate,
Tetra-n-hexyl-2-fluoroformamidinium trifluoroacetate,
2-Fluoro-1,3-dimethylimidazolinium trifluoroacetate,
2-Fluoro-1,3-diethylimidazolinium trifluoroacetate,
2-Fluoro-1,3-di(n-propyl)imidazolinium trifluoroacetate,
2-Fluoro-1,3-diisopropylimidazolinium trifluoroacetate,
2-Fluoro-1,3-di(n-butyl)imidazolinium trifluoroacetate,
2-Fluoro-1,3-di(n-pentyl)imidazolinium trifluoroacetate,
2-Fluoro-1,3-di(n-hexyl)imidazolinium trifluoroacetate,
N,N-Dimethyl-N',N'-methylphenylfluoroformamidinium trifluoroacetate,
Fluoro-bis(1-piperidyl)methylium trifluoroacetate.

In these compounds, 2-fluoro-1,3-dimethylimidazolinium trifluoroacetate represented by the formula (3) is preferred in particular.

The compound represented by the formula (1) in the invention can be prepared by the reaction of the compound represented by the above formula (4) with a metal salt of trifluoroacetic acid.

The compound represented by the above formula (4) which can be used for the raw material of the compound in the invention can be obtained in safety and with ease by carrying out a halogen exchange reaction of a compound represented by the formula (5);

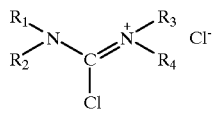

(5)

wherein $R_1$ to $R_4$ are a substituted or unsubstituted, saturated or unsaturated alkyl group, or a substituted or unsubstituted aryl group and can be the same or different. $R_1$ and $R_2$ or $R_3$ and $R_4$ can bond to form a ring containing a nitrogen atom or a nitrogen atom and other hetero atoms, and $R_1$ and $R_3$ can bond to form a ring containing a nitrogen atom or a nitrogen atom and other hetero atoms, and a chlorine anion can covalently bond with a carbon atom having a chlorine atom, with an alkali metal salt of fluorine in an inert solvent.

The term inert solvent used in the reaction refers to a solvent, which gives no influence on preparation of the compound and also does not react with raw material and product.

The alkali metal salt of fluorine which can be used for the halogen exchange reaction includes cesium fluoride, rubidium fluoride, potassium fluoride, and sodium fluoride, preferably spray dried potassium fluoride used for a fluorination reaction in view of advantage in economy and reaction efficiency.

The compound represented by the formula (5) can be prepared by chlorinating tetraalkylurea or tetraalkylthiourea with phosgene, thionyl chloride, phosphorus trichloride or other chlorinating agents. For example, 2-chloro-1,3-dimethylimidazolinium chloride can be prepared in easy by the process described in TOKUKAI HEI 59-25375.

When the compound of the invention is used as a trifluoroacetoxylation agent, the compound represented by the formula (5) can be recovered and reused after finishing the reaction in the form of tetraalkylurea or tetraalkylthiourea which is a raw material.

The above process affords the compound represented by the formula (4);

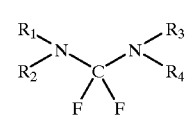

(4)

wherein $R_1$ to $R_4$ are the same as above and one of the fluorine atoms can form an ion pair as anion, preferably the compound represented by the formula (4-1);

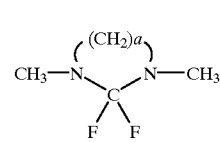

(4-1)

wherein a is an integer of 2 or 3, more preferably the compound represented by the formula (4-2);

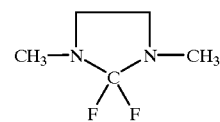

(4-2)

In the preparation process of the invention, the above-obtained compound represented by the formula (4) reacts with an alkali metal salt of trifluoroacetic acid.

The alkali metal salt of trifluoroacetic acid, which can be used for the preparation of the compound represented by the formula (1) in the invention, includes sodium trifluoroacetate and potassium trifluoroacetate.

The amount of the alkali metal salt of trifluoroacetic acid is preferably one equivalent or more, more preferably 1.1 to 1.5 equivalents for the compound represented by the formula (4).

No particular restriction is imposed upon the reaction solvent for use so long as the solvent does not react with the compound represented by the formula (4) and the formed compound. Preferred solvents include acetonitrile, 1,3-dimethyl-2-imidazolidinone, sulfolane, dichloromethane and ethylene dichloride.

No particular limitation is imposed upon the amount of the reaction solvent. The amount preferably used is 1 to 10 times by weight for the amount of the reaction material in view of reaction efficiency and workability.

The reaction temperature is in the range of 0 to 100° C., preferably 20 to 60° C. in view of a reaction velocity and stability of the product.

The reaction time is usually 5 to 15 hours, preferably, 7 to 10 hours.

The compound of the invention can be prepared under the above reaction conditions.

The compound of the invention is extremely useful as a trifluoroacetoxylation agent and can introduce a trifluoroacetoxyl group effectively with safe and ease into a compound.

For example, a hydroxyl group can be trifluoroacetoxylated by using the compound represented by the formula (1). In the reaction, the amount of the compound represented by the formula(1) is usually 1 equivalent or more, preferably 1.01 equivalents or more for the amount of the hydroxyl group.

No particular restriction is put upon the reaction solvent in the trifluoroacetoxylation so long as the solvent does not react with the compound represented by the formula (1), the compound having a hydroxyl group and the reaction product.

Preferred reaction solvents include acetonitrile, 1,3-dimethyl-2-imidazolidinone, sulfolane, dichloromethane and ethylene dichloride.

The temperature of trifluoroacetoxylation reaction is usually in the range of −20 to 150° C., preferably 0 to 100° C.

A hydrogen halogenide capturing agent, base or acid catalyst can be added in the reaction so long as giving no adverse effect on the compound represented by the formula (1), the compound having a hydroxyl group and the reaction product.

The compound formed by the reaction can be separated from the reaction mass by distillation or extraction.

The compound represented by the formula (1) can be recovered after finishing the reaction in the form of a urea derivative which is a raw material of the compound represented by the formula (5), and is thus advantageous in industry.

EXAMPLE

The present invention will hereinafter be illustrated further in detail by way of examples.

However, these examples are not construed to limit the scope of the invention.

In Example 1, the concentration of 2-fluoro-1,3-dimethylimidazolinium trifluoroacetate (hereinafter referred to simply as DMFT) in an acetonitrile solution was evaluated by reacting DMFT with aniline and measuring the resultant derivative by high performance liquid chromatography (hereinafter referred to simply as HPLC).

The concentration of fluorine ion (hereinafter referred to simply as F-) was measured by absorptiometry using an alizarin-complexon reagent.

Example 1

Synthesis of 2-fluoro-1,3-dimethylimidazolinium trifluoroacetate(DMFT)

To 40.62 g of an acetonitrile solution of 2,2-difluoro-1,3-dimethylimidazolidine(DFI) (DFI:5.21 g, 0.0383 mole), 5.21 g (0.0383 mole) of sodium trifluoroacetate was added and reacted in nitrogen atmosphere at room temperature for 7.5 hours.

After finishing the reaction, the turbid reaction mixture was filtered and the concentration of DMFT in the filtrate was measured by HPLC. The concentration of DMFT was 4.31 wt %, the yield was 71.8%.

The product had following properties.

$^1$H—NMR ($\delta$, ppm, CH$_3$CN solvent, CH$_3$CN reference, 25° C.): 3.01 (s, 6H, —CH$_3$×2), 3.91(d, J=2.5 Hz, 4H, —CH$_2$CH$_2$—), $^{13}$C—NMR($\delta$, ppm, CH$_3$CN solvent, DMSO d$_6$ reference, 23° C.): 31.0(s, —CH$_3$×2), 46.6(s, —CH$_2$CH$_2$—), 117.2(q, J=296 Hz, CF$_3$), 157.7(d, J=281 Hz, C—F), 158.9(q, J=31 Hz, C=0).

Example 2

Synthesis of n-octyl trifluoroacetate

To 40.62 g of an acetonitrile solution of 2,2-difluoro-1,3-dimethylimidazolidine (DFI) (5.21 g, 0.0383 mol as DFI), 5.21 g (0.0383 mol) of sodium trifluoroacetate was added and reacted in nitrogen atmosphere at room temperature for 7.5 hours.

After finishing the reaction, the turbid reaction mixture was filtered to obtain 8.62 g of filtrate having a DMFT concentration of 14.31 wt %, that is, 1.23 g (5.3 m mol) of DMFT. To the filtrate, 0.69 g (5.3 m mol) of n-octylalcohol was added and reacted for 7 hours at the refluxing temperature of acetonitrile.

The yield of n-octyl trifluoroacetate was 88.3% by GC analysis of the reaction mixture.

Example 3

Synthesis of benzyl trifluoroacetate

To 40.62 g of an acetonitrile solution of 2,2-difluoro-1,3-dimethylimidazolidine (DFI) (5.21 g, 0.0383 mol as DFI), 5.21 g (0.0383 mol) of sodium trifluoroacetate was added and reacted in nitrogen atmosphere at the room temperature for 7.5 hours.

After finishing the reaction, the turbid reaction mixture was filtered to obtain 8.62 g of filtrate. The filtrate had a DMFT concentration of 14.31 wt %, that is, 1.23 g (5.3 m mol) of DMFT.

To the filtrate, 0.57 g (5.3 m mol) of benzylalcohol was added and reacted for 7 hours at the refluxing temperature of acetonitrile.

The yield of benzyl trifluoroacetate was 91.2% by GC analysis of the reaction mixture.

What is claimed is:

1. A compound represented by the formula (1);

$$\begin{array}{c} R_1 \\ \phantom{R_1}\diagdown \\ \phantom{R_1R_1}N\phantom{xx}\diagup^+\phantom{x}R_3 \\ \phantom{xxxxxx}\diagdown C \diagdown N \\ R_2\diagup\phantom{xxxxxxx}\diagdown R_4 \\ \phantom{xxxxxx}| \\ \phantom{xxxxxx}F \end{array} \quad CF_3COO^- \qquad (1)$$

wherein R$_1$ to R$_4$ are a substituted or unsubstituted, saturated or unsaturated alkyl group or a substituted or unsubstituted aryl group and are the same or different, R$_1$ and R$_2$ or R$_3$ and R$_4$ are separate groups or form a heterocyclic ring, and R$_1$ and R$_3$ are separate groups or form a heterocyclic ring.

2. A compound according to claim 1 wherein the compound represented by the formula (1) is a compound represented by the formula (2);

$$\begin{array}{c} \phantom{xxx}(CH_2)a \\ \phantom{xxx}\diagup\phantom{xxx}\diagdown \\ CH_3-N\phantom{xx}\diagup^+ N-CH_3 \quad CF_3COO^- \\ \phantom{xxxxxx}\diagdown C \diagup \\ \phantom{xxxxxx}| \\ \phantom{xxxxxx}F \end{array} \qquad (2)$$

wherein a is integer 2 or 3.

3. A compound according to claim 1 wherein the compound represented by the formula (1) is 2-fluoro-1,3- dimethylimidazolinium trifluoroacetate represented by the formula (3);

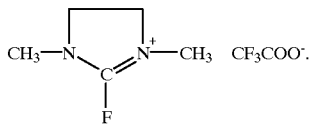
(3)

4. A preparation process of a compound represented by the formula (1);

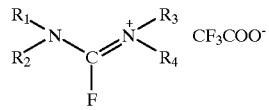
(1)

wherein $R_1$ to $R_4$ are a substituted or unsubstituted, saturated or unsaturated alkyl group or a substituted or unsubstituted aryl group and are the same or different, $R_1$ and $R_2$ or $R_3$ and $R_4$ are separate groups or form a heterocyclic ring, and $R_1$ and $R_3$ are separate groups or form a heterocyclic ring, comprising reacting a compound represented by the formula (4);

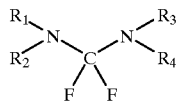
(4)

wherein $R_1$ to $R_4$ are the same as above and one of the fluorine atom can form an ion pair as anion, with an alkali metal salt of trifluoroacetic acid.

5. A preparation process according to claim 4 wherein the compound represented by the formula (1) is a compound represented by the formula (2);

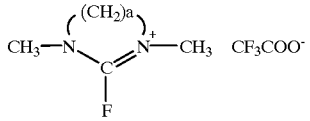
(2)

wherein a is an integer 2 or 3, and the compound represented by the formula (4) is a compound represented by the formula (4-1);

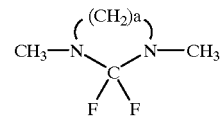
(4-1)

wherein a is an integer of 2 or 3.

6. A preparation process according to claim 4 wherein the compound represented by the formula (1) is a compound represented by the formula (3);

$$\underset{CH_3-N\underset{\underset{F}{|}}{\overset{}{C}}=\overset{+}{N}-CH_3\quad CF_3COO^-}{}$$
(3)

and the compound represented by the formula (4) is a compound represented by the formula (4-2);

$$\underset{CH_3-N\underset{F\quad F}{\overset{}{C}}N-CH_3.}{}$$
(4-2)

7. A method of introducing a trifluoroacetoxyl group in a compound having a hydroxyl group comprising reacting said compound having a hydroxyl group with the compound of claim 1.

8. A method of introducing a trifluoroacetoxyl group in a compound having a hydroxyl group comprising reacting said compound having a hydroxyl group with the compound of claim 2.

9. A method of introducing a trifluoroacetoxyl group in a compound having a hydroxyl group comprising reacting said compound having a hydroxyl group with the compound of claim 3.

* * * * *